US005230334A

United States Patent [19]
Klopotek

[11] Patent Number: 5,230,334
[45] Date of Patent: Jul. 27, 1993

[54] METHOD AND APPARATUS FOR GENERATING LOCALIZED HYPERTHERMIA

[75] Inventor: Peter J. Klopotek, Framingham, Mass.

[73] Assignee: Summit Technology, Inc., Waltham, Mass.

[21] Appl. No.: 823,816

[22] Filed: Jan. 22, 1992

[51] Int. Cl.$^5$ .............................................. A61N 5/00
[52] U.S. Cl. ............................. 128/399; 128/24 AA
[58] Field of Search ..................... 128/660.03, 662.05, 128/662.06, 24 A, 399, 804; 606/1, 27, 28, 32

[56] References Cited

U.S. PATENT DOCUMENTS

| | | | |
|---|---|---|---|
| 4,315,514 | 2/1982 | Drewes et al. | 128/660.03 X |
| 4,381,007 | 4/1983 | Doss | 128/303 |
| 4,461,294 | 7/1984 | Baron | 128/303 |
| 4,546,771 | 10/1985 | Eggletone et al. | 128/662.05 X |
| 4,580,559 | 4/1986 | L'Esperance | 128/303 |
| 4,907,585 | 3/1990 | Schachar | 606/28 |
| 4,976,709 | 12/1990 | Sand | 606/5 |

FOREIGN PATENT DOCUMENTS

| | | |
|---|---|---|
| 8906519 | 7/1989 | PCT Int'l Appl. |
| 822407 | 8/1987 | U.S.S.R. |

OTHER PUBLICATIONS

Lele et al., "Temperature Distributions in Tissues During Local Hyperthermia By Stationary or Steered Beams of Unfocused or Focused Ultrasound", Br. J. Cancer (1982) 45, Suppl. V, 108.
Hahn et al., "Induction of Hyperthermia By Ultrasound", Bulletin Du Cancer, 1981, vol. 68, No. 3.
Lehman et al., "Selective Heating Effects of Ultrasound in Human Beings", Archives of Physical Medicine & Rehabilitation, Jun. 1966.
Dickinson, "An Ultrasound System for Local Hyperthermia Using Scanned Focused Transducers" IEEE Transactions On Biomedical Engineering, vol. BME-31, No. 1, Jan. 1984.
Nyborg et al., "Temperature Elevation in A Beam Of Ultrasound", Ultrasound in Med. & Bio. vol. 9, No. 6, pp. 611–620, 1983.
Munro et al., "The Development of Improved Ultrasound Heaters Suitable For Superficial Tissue Heating", Medical Physics, vol. 9, No. 6, Nov./Dec. 1982.
Rutzen et al., "Production of Corneal Lesions Using High-Intensity Focused Ultrasound", Cornea 9(4):324–330, 1990.
S. E. P. Burgess et al., "Histologic Changes in Porcine Eyes Treated with High-Intensity Focused Ultrasound", Ann. Ophthalmol., 1987, 19:133–138.
Fessenden, "Ultrasound Methods for Inducing Hyperthermia", Font. Radiat. Ther. Onc., vol. 18, pp. 62–69 (Karger, Basel 1984).
Mainster (1979) Investigative Ophthalmology & Visual Science 18/4:416–420.
Doss et al. (1978) Los Alamos Scientific Laboratory Informal Report.
Gasset et al. (1975) Amer. Journ. of Ophthalmology 79/2:226–232.
Mainster et al. (1970) Applied Optics 9/3:665–667.
Horn et al. (1990) J. Cataract Refract Surg 16:611–616.
Stern et al. (1988) Ophthalmology 95:1434–1441.
Doss et al. (1980) Contact and Intraocular Lens Medical Journal 16/1:13–17.
Stringer et al. (1964) Nature 204:1307.
Kanoda et al. (publisher and publication date unknown).
Rowsey et al. (1980) Contact & Intraocular Lens Med. Journ. 6/1:1–12.

*Primary Examiner*—Francis Jaworski
*Attorney, Agent, or Firm*—Thomas J. Engellenner

[57] ABSTRACT

Ultrasound generating methods and apparatus are disclosed for producing controlled, localized hyperthermia in a selected heating zone of human tissue, utilizing at least one ultrasound transducer, preferably driven by sinusoidal excitation signals in a continuous wave or quasi-continuous wave mode to generate ultrasound. The temperature in the heated zone can be controlled by selecting the power, duration and frequency of the ultrasound. The penetration of the ultrasound, and thus the depth and volume of the target zone, can be controlled by selecting the excitation frequencies so to confine the absorption of the ultrasound beam in the target tissue. The invention is particularly useful in inducing controlled collagen shrinkage in corneal tissue to effective thermokeratoplasty (heat induced modification of the shape of the cornea).

16 Claims, 2 Drawing Sheets

METHOD AND APPARATUS FOR GENERATING LOCALIZED HYPERTHERMIA

BACKGROUND OF THE INVENTION

The technical field of this invention is high frequency ultrasonic, or hypersonic, therapy and, in particular, the use of such therapies for thermokeratoplasty (heat-induced modifications of the shape of the cornea) and other surgical procedures based on controlled hyperthermia.

In recent years, researchers have developed a wide range of therapeutic and surgical procedures utilizing the application of localized hyperthermia at selected target sites within human patients. These techniques include destruction of tumors, ophthalmological procedures, such as eye thermokeratoplasty, and sealing of small blood vessels to reduce bleeding during surgery. Various types of apparatus have been employed to deliver this localized heat, including torches, heated needles, electric scalpel, microwave devices, lasers, and ultrasound generators.

The predictability, controllability and safety of thermokeratoplasty and other hyperthermia procedures is largely dependent upon accurate control of the location and temperature of the hyperthermia zone in the human tissue, as well as the duration of the heating. In particular, the success of many hyperthermia-based surgical and therapeutic procedures requires precise control of the space/time profile of the hyperthermia applied to the target tissue. An additional requirement is the avoidance of excessive overheating of, and damage to, surrounding tissue.

Appreciation of these requirements has led many researchers to the conclusion that virtually all conventional hyperthermia techniques have serious shortcomings. In particular, it is impracticable to utilize a thermal source to selectively deliver heat to target volumes of tissue through thermal diffusion, because when the distal portions of the volume are heated to the desired temperature, severe overheating of the tissue in direct contact with the source occurs.

Laser thermokeratoplasty methods offer alternatives to conventional, physical contact hyperthermia. Such techniques involve the application of a beam of infrared radiation into the tissue volume. However, the application of infrared lasers to generate localized heating often relies upon the balancing of intensity enhancement in a focused laser beam and the optical attenuation presented by tissue material, factors that sometimes are not precisely controllable. In addition, the laser approach is expensive and requires a large supporting apparatus.

It is, accordingly, an object of the invention to provide improved methods and apparatus for generating hyperthermia.

It is another object of the invention to provide hyperthermia methods and apparatus utilizing a source of radiation that deposits energy into tissue in a controllable manner.

Other general and specific objects of the invention will in part be obvious and will in part appear hereinafter.

SUMMARY OF THE INVENTION

The foregoing objects are attained by the invention, which provides ultrasound, generating methods and apparatus for producing controlled, localized hyperthermia in human tissue. The term "ultrasound" as used herein is intended to encompass both conventional "ultrasound" as typically used to describe high-frequency acoustic waves up to about 100 megahertz and "hypersound" as typically used to describe very high-frequency acoustic waves greater than 100 megahertz. In general, "ultrasound" is used hereto to describe acoustic waves capable of inducing controlled hyperthermia in biological tissue, particularly the corneal tissue of the eye.

In accord with one aspect of the invention, the apparatus includes at least one ultrasound transducer that can be driven by electrical excitation signals to generate ultrasound. The apparatus can also include one or more propagation elements, for example, focusing elements for focusing the ultrasound beam generated by the transducer and elements that direct and control the size and shape of the ultrasound beam into the target tissue.

In one embodiment, the excitation elements drive the ultrasound transducer to generate ultrasound having a sinusoidal excitation and in a continuous wave or quasi-continuous mode. Ultrasound, as generated by the transducer, is focused by the focusing elements, or focusing surface, and transmitted through a ultrasound transmitting crystal and acoustical matching medium to generate heat in the target tissue.

In another aspect of the invention, a controller is provided for selecting a range of ultrasound frequencies, thereby controlling the spatial parameters of the heated volume. For example, the electronics control module can cause the excitation elements to sweep through a selected range of ultrasound frequencies. Preferably, this range begins at higher frequencies, approximately 500 MHz, and ends at lower frequencies, at approximately 20 MHz.

In further aspects of the invention, the amplitude and/or duration of the ultrasound beam can be selected. The spatial dimensions and position of the ultrasound apparatus, such as the separation between the ultrasound generating source and the target tissue, or the focusing volume (f-number) of the ultrasound beam, can also be selected. The symmetry of the ultrasound beam, in addition, can be selected by applying a non-circular beam of ultrasound to the target tissue.

According to yet a further aspect of the invention, control elements are provided for selecting various hyperthermia parameters, such as the desired temperature of the hyperthermia zone, the volume of the heated zone within the target tissue and the penetration depth, as well as for selecting the frequency profile and combination necessary to deposit a dedicated portion of the beam energy at a desired location and depth within the hyperthermia zone.

Another aspect of the invention involves methods for performing thermokeratoplasty and similar surgical procedures. According to this aspect, ultrasound is generated and directed into the corneal target tissue. The ultrasound beam is controlled to deposit the energy into the stroma region of the cornea, at approximately 300 to 450 micrometers or less in depth, to cause the collagenous tissue to shrink, thereby changing the refractive power of the corneal surface.

The invention will next be described in connection with certain illustrated embodiments; however, it should be clear to those skilled in the art that various modifications, additions and subtractions can be made without departing from the spirit or scope of the claims.

BRIEF DESCRIPTION OF THE DRAWINGS

For a further understanding of the nature and objects of the invention, reference should be made to the following detailed description and the accompanying drawings, in which.

DETAILED DESCRIPTION

Figure 1:
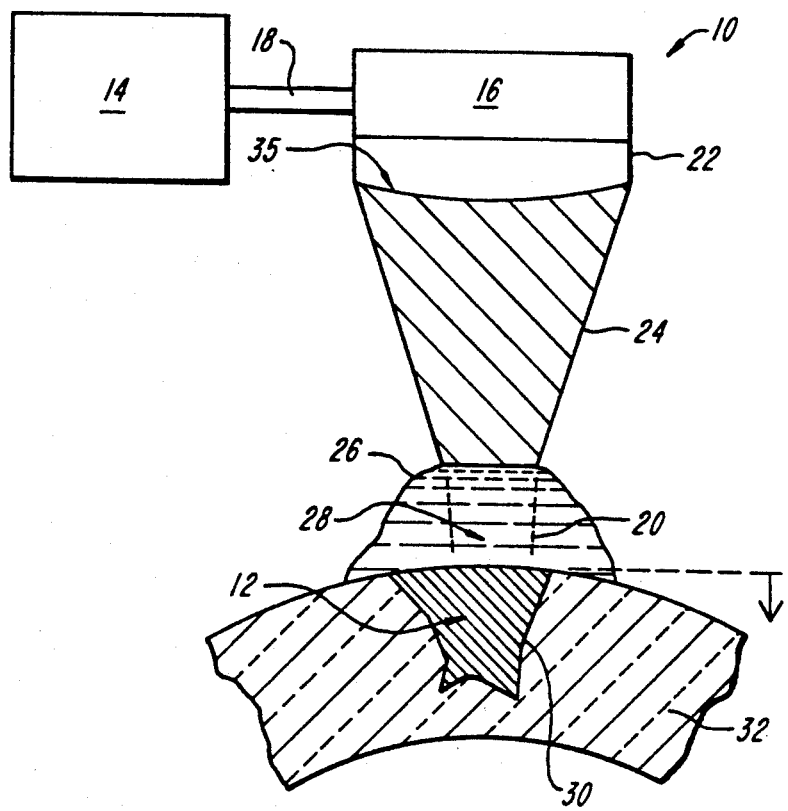
FIG. 1 is a schematic diagram depicting ultrasound generating apparatus constructed in accord with the invention, for producing controlled, localized hyperthermia in human tissue.

FIG. 1 is a schematic diagram depicting an ultrasound generating apparatus 10, constructed in accord with the invention, for producing controlled, localized hyperthermia in human target tissue 12. The apparatus of FIG. 1 shows an electronic control module 14 in communication with a transducer element 16 through communication lines 18. The apparatus generates a ultrasound beam, or wavefront 20, and can include a transducer 16, focusing element(s) 22, an acoustically-transmitting waveguide 24, and an acoustical coupling medium 26. The beam of ultrasound 20 strikes the target tissue 12 at a selected site 28 to create a hyperthermal zone 30 within a define volume of tissue. In particular, the illustrated system 10 can be utilized to modify the shape of the cornea 32 of the human eye, by generating heat in a hyperthermia zone 30 at target tissue 12 at selected depth penetration 34 within the cornea 32. Although the shape of the focusing element 22 is illustrated as planoconvex, various other shapes can be used for particular application, including convex, planoconcave, concave and combinations of such shapes. Moreover, the focusing means 22 need not be a separate physical element but instead can be formed as a surface or portion of the transducer 16.

While the embodiment depicted in FIG. 1 is adapted for performing ultrasound thermokeratoplasty and other surgical procedures on the eye, those skilled in the art will appreciate that the invention can be utilized in other therapeutic procedures and can be practiced in connection with other configurations suitable for generating and applying ultrasound hyperthermia to other regions of the body.

The invention is based upon the recognition that precise control of the hyperthermia procedures can be achieved in a system utilizing ultrasound radiation. In one embodiment, high frequency ultrasound, e.g., ranging from about 1 MHz to about 1 GHz in frequency, can be controlled and applied for surgical purposes in the manner discussed hereinafter. Unlike the use of laser radiation in laser thermokeratoplasty, the frequency (or wavelength) of ultrasound waves can be varied easily. Since the acoustic absorption coefficient of irradiated tissue will vary significantly with the frequency of the applied ultrasound, the present invention permits additional control over the absorption/penetration depth of the ultrasound beam.

More particular, and as indicated in FIG. 1, the system includes at least one ultrasound transducer 16 for generating ultrasound in a known manner in response to electrical excitations applied thereto. The system can also include a curved surface 35 for focusing of the ultrasound beam 20 generated by the transducer 16, an ultrasound conducting element 24, and an acoustical coupling medium 26, e.g., a biocompatible hydrogel or aqueous solution which approximates the acoustic properties of the tissue.

The transducer 16 can be of conventional design and may include, for example, a conventional PVDF transducer element. Alternatively, the transducer 16 can be constructed of other materials, including crystalline quartz, or piezoelectric materials, such as zirconium titanite, lithium noibide, or a lead zirconium.

In accordance with the invention, electrical excitation from the controller 14 is employed to drive the transducer 16, e.g., with a sinusoidal excitation in a continuous wave mode, to generate ultrasound. The term "continuous wave" or "CW" is used hereto do denote both continuous and quasi-continuous waves, as well as other similarly periodic forms of excitation. The ultrasound beam 20, thus generated by the transducer 16, is focused by a focusing element 22 and conducted by ultrasound transmitting element 24 through medium 26 to generate a hyperthermia zone 30 at eye tissue 12. In thermokeratoplasty procedures according to the invention, the hyperthermia zone 30 is preferably confined primarily to the anterior region of the stroma (e.g., to a depth of about 350 microns or less in the corneal tissue).

The diameter of the hyperthermia zone 28 can be controlled by a number of criteria, including the radius of the focusing surface 22, the distance between target tissue 12 and the focusing element 22, and the diameter of the lower output surface of the ultrasound transmitting crystal 24. The temperature in the hyperthermia zone 30 of target tissue 12 can be controlled by selecting the power, duration, and constituent frequencies of the ultrasound beam 20.

Moreover, as shown in FIG. 1, the depth of ultrasound penetration 34 within the hyperthermia volume 30 can be controlled by a control module 14, which applies selected excitation frequencies to the transducer 16 through signal lines 18. The selected frequencies induce hypersonic waves in the transducer 16 and, as discussed in greater detail hereinafter, determine ultrasound penetration depths in accordance with the ultrasound absorption characteristics of the target tissue 12.

In one preferred embodiment, the ultrasound waves lie in a frequency range from about 10 MHz to about 1 GHz, and, more preferably, from about 20 MHz to about 500 MHz, within a regime often referred to as "hypersound." Physically, hypersound waves lie between lower frequency ultrasound, which is characterized by large penetration depths and small attenuation, and thermal phonons, which are quantum mechanical sound waves of extremely high frequencies. Hypersound is also strongly scattered. Thus, analogous to thermal phonon behavior, hypersound has limited absorption depth. However, unlike the characteristics of the heat diffusion, hypersound can be directed. Moreover, the wave-like transport process of hypersound radiation is not governed by diffusion. Simple ray-tracing, with additional absorption coefficient information, can be utilized to model and analyze hypersound penetration of tissue.

The illustrated system 10 shown in FIG. 1 can provide controllable heating, with little heating beyond 60°-70° C. The cumulative duration of the hyperthermia can be limited to a few seconds, without excessive overheating in any single region.

Figure 2:
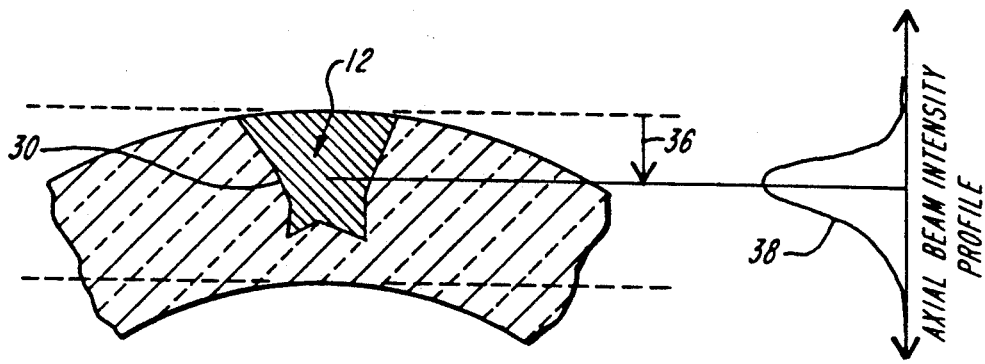
FIG. 2 is a schematic cross-sectional view of a cornea depicting controlled heating depth in the heated volume and the axial profile of the energy deposited by the ultrasound beam.

FIG. 2 illustrates the correlation between the target tissue hyperthermia zone 30 and the hypersound waves. FIG. 2 also shows, in a sideways mapping, the correlation between the desired spatial depth 36 of the hyperthermia volume 30 and the region of maximum heating. As the concentration of the acoustic beam 38 increases, the power density (power/unit volume) created by overlapping ultrasound waves also increases. Heating is directly related to the power density applied to the volume 30. Thus, by the selective application of multiple frequencies to the characteristic absorption of the target tissue 12, ultrasound can create a maximum heating zone at a desired depth 36 and temperature.

This concentration of the acoustic beam is analogous to the focusing effect of a lens on optical beams, such that the spatial location of the peak beam concentration 36 is tightly controlled.

Figure 3:
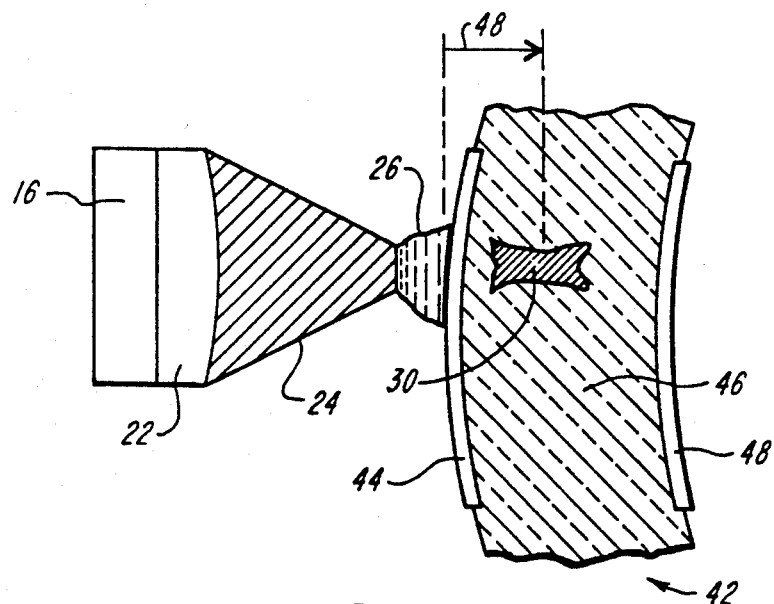
FIG. 3 is a schematic diagram of another embodiment of the present invention, as applied to heating the cornea of an eye.

FIG. 3 illustrates an embodiment of the invention for applying ultrasound hyperthermia to a human eye. The cornea 42 includes several layers, including the anterior epithelium and Bowman's layer 44, the collagenous stroma 46, and Descemet's membrane and the posterior endothelium 48.

The invention selectively shrinks the collagen fibers in the cornea 42 by the use of ultrasound hyperthermia, without heating damage to the delicate areas outside the stroma 46. In a manner similar to that discussed above in connection with FIG. 1, the ultrasound beam from transducer 16 is focused by the focusing element 22, transmitted through the ultrasound transmitter element 24 and through an acoustical medium 26, to create the hyperthermia zone 30 in the collagenous tissue 46. The contracted fibers cause the heated regions of the cornea 42 to pucker slightly, thereby changing the refractive properties of the cornea 42.

The human cornea has a thickness of approximately 500 microns. In pure water at a temperature T=30° C., the absorption depth for ultrasound at a frequency of 139 MHz is approximately 100 microns. Controlled overheating is, thus, attained by the system of FIG. 3 by selecting appropriate frequencies for generating the ultrasound beam in accord with these absorption characteristics. These frequencies are chosen by the controller, such that the energy is absorbed at a desired spatial depth 48 to control the hyperthermia volume 30 within the collagenous tissue 46. The depth 48 of the hyperthermia volume 30 within the cornea 42 should be limited for safety reasons to less than 80% of the corneal thickness.

Figure 4:
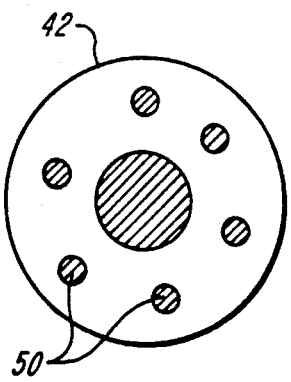
FIG. 4 is a schematic diagram that exemplifies the application of ultrasound hyperthermia for hyperopic correction.

FIG. 4 depicts repeated application of ultrasound hyperthermia 50 to the cornea 42 in a ring configuration for hyperoptic correction. The ring configuration of coagulation spots 50 are formed about the eye's optical axis. Larger hyperoptic corrections can be made through the application of more concentric ring patterns.

Figure 5:
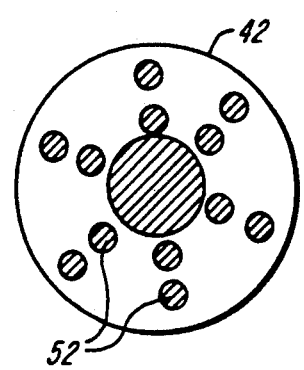
FIG. 5 is a schematic diagram that exemplifies the application of ultrasound hyperthermia for myopic correction.

FIG. 5 similarly depicts a radial application of ultrasound hyperthermia 52 to the cornea 42 for myopic correction. The symmetrical radial pattern provides for the reduced optical power in the corneal profile.

Other ultrasound hyperthermia patterns correct other visual deficiencies. For instance, non-symmetric ultrasound hyperthermia applied to regions of the stroma can provide astigmatic correction. A line of coagulation spots can be used to cause a steepening of curvature along an axis. Combinations of the above patterns can also be used to correct a multiplicity of refractive errors.

It will, thus, be seen that the invention efficiently attains the objects set forth above, among those made apparent from the preceding description. In particular, the invention provides methods an apparatus for generating controlled, localized hyperthermia in selected target regions of human tissue, while reducing or avoiding damage to collateral regions of tissue.

It will be understood that changes may be made in the above construction and in the foregoing sequences of operation without departing from the scope of the invention. For example, the invention can be practiced in connection with ultrasonic or ultrasound transducers having different configurations. In addition, those skilled in the art will appreciate that the invention can be utilized in other medical applications.

It is accordingly intended that all matter contained in the above description or shown in the accompanying drawings be interpreted as illustrative rather than in a limiting sense.

It is also to be understood that the following claims are intended to cover all of the generic and specific features of the invention as described herein, and all statements of the scope of the invention which, as a matter of language, might be said to fall therebetween.

What is claimed is:

1. Apparatus for generating controlled hyperthermia in a selected hyperthermia zone in a target region of tissue in a body, the apparatus comprising:
   ultrasound generating means for generating ultrasound;
   propagation means, in acoustical communication with said ultrasound generating means, for directing the ultrasound into said target region; and
   frequency control means for selecting a plurality of frequencies of said ultrasound, from a range of about 20 MHz to 500 MHz, such that said plurality of frequencies constructively interfere within said tissue to deposit acoustic energy at a selected location within said target region.

2. Apparatus according to claim 1 wherein said ultrasound generating means includes an ultrasound transducer for generating ultrasound in response to applied electrical excitation signals.

3. Apparatus according to claim 2 wherein said ultrasound generating means includes electrical excitation means for generating and applying to said ultrasound transducer said electrical excitation signals having a substantially sinusoidal waveform in a continuous wave mode.

4. Apparatus according to claim 1 wherein said apparatus further includes focusing means for acoustically focusing said ultrasound.

5. Apparatus according to claim 1 wherein said propagation means comprises an ultrasound transmitting waveguide.

6. Apparatus according to claim 5 wherein said propagation means further comprises acoustic coupling means disposed between said waveguide and said target region.

7. Apparatus according to claim 1 wherein said frequency control means comprises means for sweeping said frequencies of said ultrasound though a selected frequency range.

8. A method for generating controlled hyperthermia in a target region of corneal tissue, the method comprising the steps of:
generating a series of waves of ultrasound having a plurality of frequencies within the range of about 20 MHz to about 500 MHz;
propagating said ultrasound into said target region of cornea tissue; and
controlling the frequency components of said ultrasound to deposit acoustical energy such that said components constructively interfere in said tissue within said target region.

9. A method according to claim 8 wherein the step of generating the ultrasound further includes electrically exciting an ultrasound transducer.

10. A method according to claim 8 wherein the step of generating the ultrasound further comprises generating a series of substantially sinusoidal, continuous waves of said ultrasound.

11. A method according to claim 8 wherein the step of propagating said ultrasound further comprises the step of acoustically focusing said ultrasound into the target region.

12. A method according to claim 8 wherein the step of propagating said ultrasound further includes the step of employing an acoustically transmitting waveguide to direct the transmission of said ultrasound.

13. A method according to claim 12 wherein the step of propagating said ultrasound further includes the step of employing an acoustic coupling element between the waveguide and the target region.

14. A method according to claim 8 wherein the step of controlling the frequency components further includes the step of sweeping through a selected range of ultrasound frequencies.

15. A method according to claim 8 wherein the method further includes the step of controlling the target region size and volume of the hyperthermia zone within the cornea to induce controlled collagen shrinkage and effect keratoplasty.

16. A method of performing corneal thermokeratoplasty, the method of comprising the steps of:
generating a series of waves of ultrasound ranging from about 20 MHz to about 500 MHz;
propagating said ultrasound toward a cornea;
focusing said ultrasound within the collagen region of said cornea; and
varying the frequency of said ultrasound to provide a plurality of frequencies and thereby generate a constructive interference hyperthermia zone within the collagen region at a selected location whereby, the collagenous tissue shrinks in a controlled manner in said hyperthermia zone, thereby modifying the shape of the cornea.

* * * * *